Figure 1:
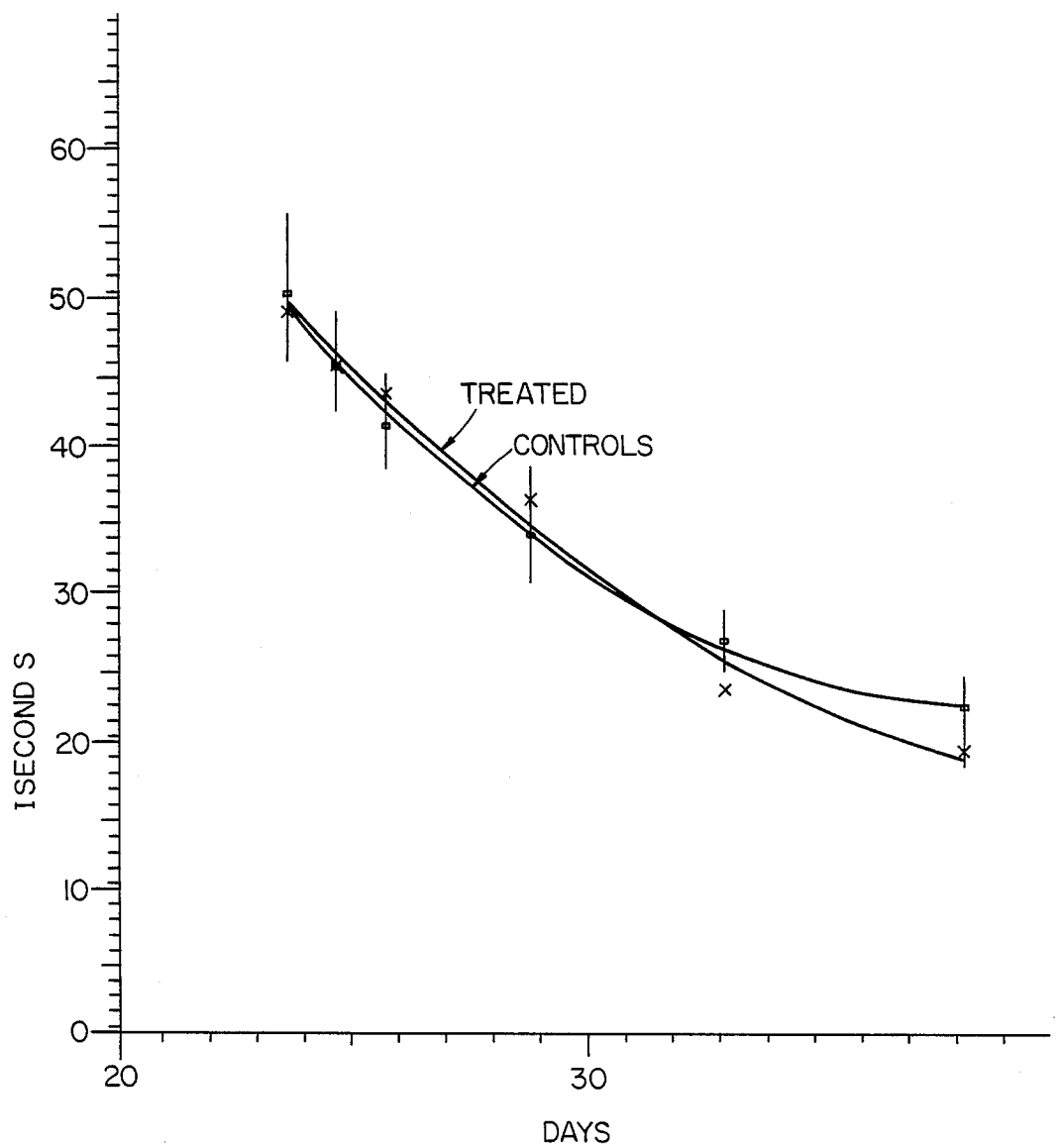
Figure 2:
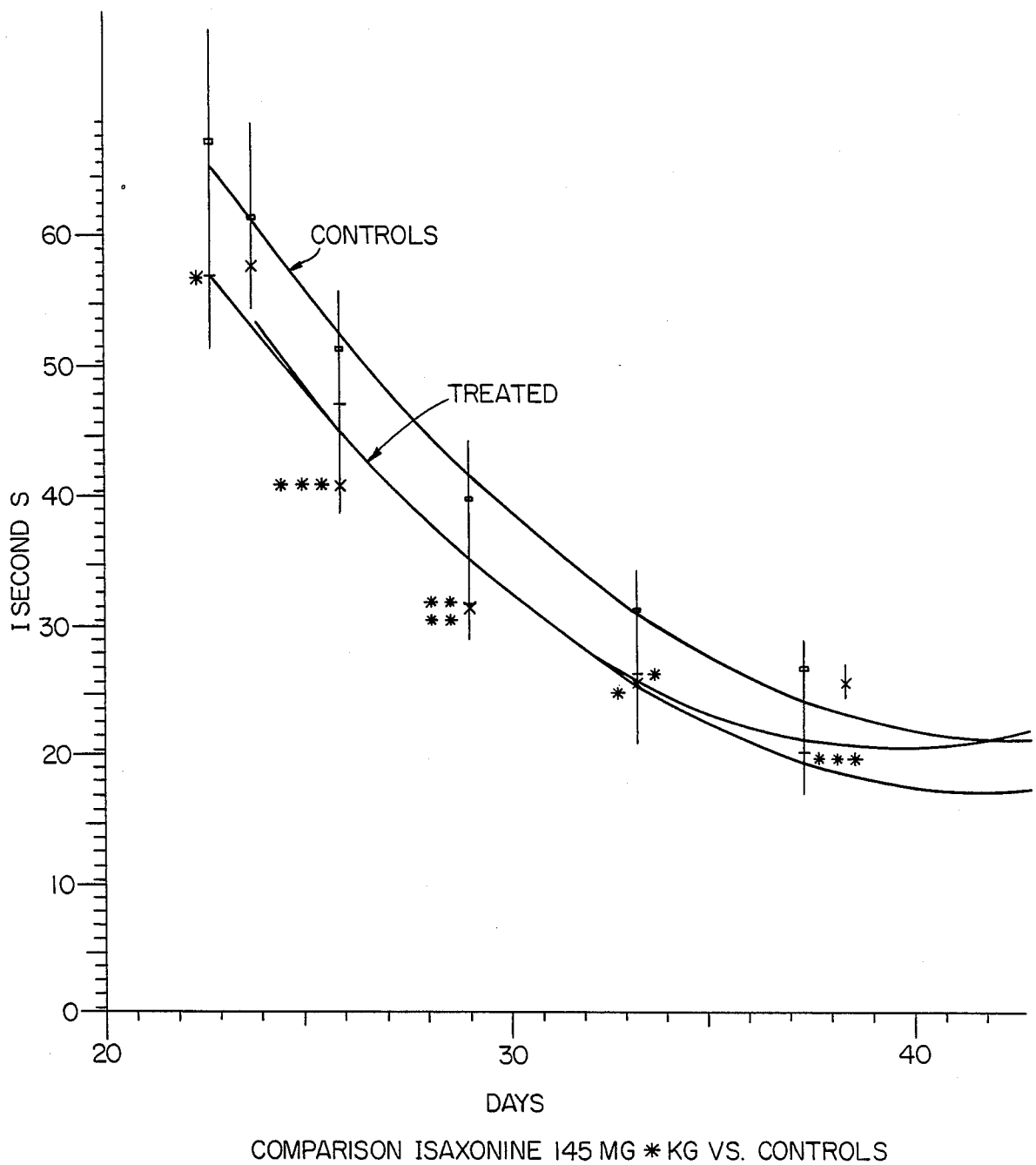

United States Patent [19]

Hugelin et al.

[11] Patent Number: 4,835,184

[45] Date of Patent: May 30, 1989

[54] NOVEL PHARMACEUTICAL COMPOSITIONS INTENDED TO THE TREATMENT OF NEUROPATHIES AND PROMOTING THE NERVOUS REGENERATION

[75] Inventors: Andre Hugelin, Neuilly S/Seine; Claude Thal, Sceaux, both of France

[73] Assignee: Albert Rolland SA, Sceaux, France

[21] Appl. No.: 893,025

[22] Filed: Aug. 1, 1986

[30] Foreign Application Priority Data

Jul. 31, 1985 [FR] France ............... 85 11664

[51] Int. Cl.[4] ........................... A61K 31/205
[52] U.S. Cl. ..................... 514/554; 514/866
[58] Field of Search ............ 514/557, 554, 556, 565, 514/866

[56] References Cited

FOREIGN PATENT DOCUMENTS 7116M 7/1969 France.

OTHER PUBLICATIONS

Chem. Abst. 107: 205192p, 1987.
Chem. Abst. 73: 972ooh, 1970.

Primary Examiner—John W. Rollins
Attorney, Agent, or Firm—Bierman & Muserlian

[57] ABSTRACT

Compositions and method of treating neuropathies resulting from diabetic, non-diabetic, toxic or viral origin and insuring regeneration of damaged nerve fibers by administration of the N,N-dimethyl-biguanide salt of p-chlorophenoxy-acetic acid.

1 Claim, 2 Drawing Sheets

NOVEL PHARMACEUTICAL COMPOSITIONS INTENDED TO THE TREATMENT OF NEUROPATHIES AND PROMOTING THE NERVOUS REGENERATION

SUMMARY

This invention relates to the field of medicinal chemistry.

More particularly it relates to pharmaceutical compositions endowed with neurotrophic capacity, the active ingredient of which is the salt of N,N-dimethyl-biguanide with p-chlorophenoxy-acetic in admixture or conjunction with an inert vehicle or carrier.

These pharmaceutical compositions according to this invention are useful for treating neuropathies and nervous degenerescence.

This invention relates to novel pharmaceutical compositions endowed with neurotrophic capacity.

More particuarly, this invention relates to pharmaceutical compositions intended to allow the growth, the conservation and the regeneration of nervous cells. The compositions according to this invention further insure a protection against neuropathies and nervous degenerescences.

This invention specifically provides novel pharmaceutical compositions endowed with neurotrophic capacity which consist in that a neurologically-active amount of the N,N-dimethyl-biguanide salt of p-chlorophenoxy-acetic acid is admixed or put in conjunction with an inert non-toxic pharmaceutically acceptable carrier or vehicle.

Some pharmaceutical compositions containing the N,N-dimethyl-biguanide salt of p-chlorophenoxy-acetic acid are already known. They are utilized under a form and a dosology suitable for treating certain kinds of diabetes and namely non insulino-dependant diabetes. For this therapy the amount of active ingredient is 500 mg and the usual dosology is from 1,000 to 1,500 mg per day per oral way.

It is also known that one of the most severe complications of diabetes lies in the occurrence of nervous degenerations which cannot be alleviated or cured using the conventional medicines of diabetes.

It has now been found and this is the basis of the present invention, that the N,N-dimethyl-biguanide salt of p-chlorophenoxy-acetic is further endowed with neurotrophic properties which contribute to counteract or decrease the serious nervous complications of the diabetes without interfering with the own treatment of this illness.

Namely on the basis of the results obtained during the pharmacological testing, it may moreover be ascertained that in non-diabetic subjects, the N,N-dimethyl-biguanide salt of p-chlorophenoxy-acetic acid also induce a neurotrophic effect which allows its use in a broad range of neuropathies from nervous or traumatic origin.

This invention thus resides in the fact that the pharmaceutical compositions containing as active ingredient the N,N-dimethyl-biguanide salt of p-chlorophenoxy-acetic acid found a therapeutic utilization in the treatment of neuropathies from diabetic or non-diabetic origin, from traumatic origin, from toxic origin or from degenerative origin.

They also found a therapeutic use in insuring the regeneration of the nervous fibres after lesion either from a therapeutic origin, immunologic origin or from a viral origin.

It may also be assumed that the pharmaceutical compositions according to this invention may also be used for preventing or curing the neuropathies inducing a damage to the neurons such it is when using some toxic drugs, for example the alkaloids of Vinca Rosea, Almitrine, Colchicine and the most part of the neuro-toxic drugs.

This novel action may be reached using a some what different dosology than that previously used for the treatment of diabetes. It appears as necessary to use markedly higher dosology, ranging in the adult man from 1.50 g and 4 g of active ingredient per day. Further the route of administration is not restricted to the digestive one. It may also administered by the parenteral or the rectal ways.

In consequence of the foregoing the pharmaceutical compositions according to this invention contain as active ingredient a neurologically active amount of the N,N-dimethyl-biguanide salt of p-chlorophenoxy-acetic acid ranging from 1,000 to 2,500 mg per unit dosage.

The most suitable pharmaceutical compositions intended for this novel use are the effervescent tablets, the chewing tablets, the drinkable solutions or the drinkable ampuls.

Among the vehicles or carriers it may more particularly be cited those which are suitable for administration by parenteral or digestive ways of administration. In this aspect it may be cited water, salines, isotonic salt solutions, solutions of polyethyleneglycol in water, aqueous solutions of polyvinylpyrrolidone for the injectable preparations, the conventional diluents such as starches, celluloses, magnesium carbonate, calcium phosphate, silica, magnesium stearate, talc for the solid forms; binding agents; sweetening agents; flavouring agents, products which improves the taste. It may further be used as suppositories or rectal soft gelatine capsules for the rectal way of administration.

This invention also extends to a process for producing the pharmaceutical compositions endowed with neurotrophic capacity which consists in that a neurologically-effective amount of the N,N-dimethyl-biguanide salt of p-chlorophenoxy-acetic acid is admixed or in conjunction with an inert non-toxic pharmaceutically-acceptable carrier or vehicle according to the known-methods of the pharmacotechnology.

The experimental part hereafter appearing is a summary of the numerous tests performed in the animals and is merely intended to explain the invention.

EXAMPLE I

Effervescent tablets containing the N,N-dimethyl-biguanide salt of p-chlorophenoxy-acetic acid:

| active ingredient | 1,500 g |
| corn starch | 24 g |
| wheat starch | 36 g |
| lactose | 375 g |
| sodium bicarbonate | 12.6 g |
| tartaric acid | 11.25 g |
| hydroxypropyl cellulose | 18 g |
| polyvinylpyrrolidone marketed under the Trade Name POVIDONE C 15 | 12 g |
| micronized saccharose | 120 g |
| for 1,000 tablets weighing in average | 2,1 g |

EXAMPLE II

Pharmacological studies with the pharmaceutical compositions according to this invention:

(A) First Test

Experimentation has been carried out in four batches of 10 male rats of Whistar strain weighing 200±5 g. The animals have been surgered at the starting day ($D_o$) after having been anesthetized with pentobarbital (40 mg/kg IP). The sciatic nerve has been congealed in three equidistant points on the same circonference of the nerve, at about the medium third of the leg by means of a cryo-sound frozen to −170°, for about 3 seconds.

The treatments have been initiated the day after ($D_1$). The amimals have been a new operated on at the seventh day ($D_{+7}$) after being anesthetized with Nembutal (20 mg/kg IP) which do not suppress either the tone of the muscles of the tail or the nociceptive reflexes of defence.

The repair of the sensitive fibres has been determined from the day $D_{+7}$ after dissection of the sciatic nerve along all its traject from the ankle to the lesion. The said regeneration has been tested through a mechanical stimulus of the nerve using a blunt clip climbing along the nerve in the distroproximal direction. The length of the regenerated fibres has been valuated by measuring the location of the point from which the first reflex nociceptive response has been got. The determinations have been performed in group of animals each receiving intraperitoneously under the same volume (1 ml):

1. saline
2. a non-buffered aqueous solution containing 145 mg/kg Isaxonine taken as reference substance
3. an aqueous solution containing 250 mg/kg of the N,N-dimethyl-biguanide salt of p-chlorophenoxy-acetic acid
4. an aqueous solution containing 250 mg/kg of N,N-dimethyl-biguanide as the hydrochloride, taken as a control.

The regenerated lenghthes have been as follows:

| | |
|---|---|
| Saline | 22.15 mm ± 0.98 (SD) |
| Isaxonine | 23.75 mm ± 1.03 (SD) |
| N,N—dimethyl-biguanide p-chlorophenoxyacetate | 23.87 mm ± 1.45 (SD) |
| N,N—dimethyl-biguanide hydrochloride | 23.00 mm ± 1.26 (SD) |

The comparison of the mean values using a test "t" indicates that regeneration is significatively increased (+7%) with N,N,-dimethyl-biguanide salt of p-chlorophenoxy-acetic acid. With N,N-dimethyl-biguanide hydrochloride the values are not statistically significant. It does not exist any significative difference in the regeneration of sensitive fibres in the treated rats with either Isaxonine or N,N-dimethyl-biguanide compared to the controls.

This indicates that the increase of 7% of the regenerated lenghth is statiscally-significative using the test "t" which does not apply to the value 7%.

(B) Second test

The speed of regeneration of the sensitive fibres after lesion of the sciatic nerve and Wallerian degeneration has been studied in batches of male rats (Whistar strain) weighing 210 g ±10 g. The right sciatic nerve has been damaged by congealing it using a cryod for cataract previously frozen to −170° C., for 30 seconds in 3 points, on a same circonference located at the upper third of the leg, i.e; 90 mm ±5 mm from the penetration of this nerve in the plantar area. The internal femoris nerve has been cut out on several centimeters. Recuperation of the sensitive feeling has been determined by measuring the latency of the somesthaesic evoked potential picked up at the level of the contralateral or homolateral primary areas using metallic extradurmerian imbedded and permanently maintained electrods. The response has been evoked by stimulating the more interal pad of the right plantar sole through an electric stroke of 5 mA released under constant power for 2 ms every 620 ms.

The mean responses have been calculated from 500 to 2,000 times with a precision of ±0.5 ms.

The latency of the earliest positive response ($P_1$) and at the lowest threshold has been determined and compared in the two groups of animals at days $D+25$, $D+29$, $D+33$, $D+38$ and $D+43$.

The controls (N=11) have been given by forcible feeding for 6 days out 7, 0.5 g/kg of a solution of arabic gum.

The group of treated rats has been given at the same times and by the same way 0.5 g/kg of the N,N-dimethyl-biguanide salt of p-chlorophenoxy-acetic acid.

The regression curves have been calculated using the method of the least squares and the averages have been compared by pairs using the test "t" of student.

The obtained results evidence an increase in the speed of the reappearance of the sensitive responses ($P_1$) in the animals treated with the N,N-dimethyl-biguanide salt of p-chlorophenoxy-acetic acid, in average of 2.5 days.

The mean values are statiscally different for each plot of the curves. Between the controls and the batch of treated animals, the comparison of the mean values by pair gives a significative difference at the level $P<0.01$ between the controls and the treated animals.

Conclusively the treatment by N,N-dimethyl-biguanide salt of p-chlorophenoxy-acetic acid precociously induces, from the day $D+25$, a negative response $N_1$ at higher level that the response $P_1$, which cannot be evidenced in the controls before the 50th day after the lesion.

These results led to the conclusion that the N,N-dimethyl-biguanide salt of p-chlorophenoxy-acetic acid has a strong action on the regeneration of the nervous fibres in the mammals.

What we claim is:

1. A method for treating the neuropathies from diabetic, nondiabetic, toxic or viral origin and promoting the regeneration of damaged of nervous-fibres which comprising administering to patients suffering from said neuropathies a safe but efficient amount of the N,N-dimethyl-biguanide salt of p-chlorophenoxy-acetic acid.

* * * * *